(12) United States Patent
Wang

(10) Patent No.: US 10,139,263 B2
(45) Date of Patent: Nov. 27, 2018

(54) METHOD TO CALIBRATE DISPOSABLE CARTRIDGE CUVETTE THICKNESS IN-SITU

(71) Applicant: Honeywell International Inc., Morristown, NJ (US)

(72) Inventor: Tzu-Yu Wang, Maple Grove, MN (US)

(73) Assignee: Honeywell International Inc., Morris Plains, NJ (US)

( * ) Notice: Subject to any disclaimer, the term of this patent is extended or adjusted under 35 U.S.C. 154(b) by 567 days.

(21) Appl. No.: 13/794,241

(22) Filed: Mar. 11, 2013

(65) Prior Publication Data

US 2014/0256056 A1    Sep. 11, 2014

(51) Int. Cl.
| | | |
|---|---|---|
| *G01N 21/05* | (2006.01) | |
| *G01F 25/00* | (2006.01) | |
| *G01N 21/11* | (2006.01) | |
| *G01N 21/45* | (2006.01) | |

(52) U.S. Cl.
CPC ......... *G01F 25/0084* (2013.01); *G01N 21/05* (2013.01); *G01N 21/11* (2013.01); *G01N 21/45* (2013.01)

(58) Field of Classification Search
CPC .................................................. G01B 11/2441
USPC ........................................................... 422/50
See application file for complete search history.

(56) References Cited

U.S. PATENT DOCUMENTS

| | | | |
|---|---|---|---|
| 6,545,765 B1* | 4/2003 | Ganser et al. ................ 356/632 |
| 7,742,164 B1* | 6/2010 | Phillips et al. ............ 356/243.2 |
| 2003/0025899 A1* | 2/2003 | Amara et al. .................... 356/73 |
| 2011/0229897 A1* | 9/2011 | Bell et al. ..................... 435/6.12 |
| 2012/0231534 A1* | 9/2012 | Carroll et al. ............. 435/288.7 |

* cited by examiner

*Primary Examiner* — Lyle Alexander
*Assistant Examiner* — Emily R. Berkeley
(74) *Attorney, Agent, or Firm* — Schwegman Lundberg & Woessner, P.A.

(57) ABSTRACT

An analytical system includes a laser disposed to direct light toward a microfluidic feature disposed in a feature layer of a multiple layer test cartridge, a sensor to receive reflections from capping layers disposed about the microfluidic feature in the feature layer, and a controller to determine a depth of the microfluidic feature as a function of the received reflections.

11 Claims, 5 Drawing Sheets

METHOD TO CALIBRATE DISPOSABLE CARTRIDGE CUVETTE THICKNESS IN-SITU

BACKGROUND

Geometric variability in disposable devices due to manufacturing tolerances can negatively impact performance to the extent that a product or process may not meet sufficient regulatory or industry standard requirements. Where this can present a special problem includes processes that depend on quantization in a volume or thickness related to a microfluidic test cartridge fluidic channel. While there may be a variety of solutions, many may be costly or otherwise difficult to implement.

SUMMARY

An analytical system includes a laser disposed to direct light toward a microfluidic feature disposed in a feature layer of a multiple layer test cartridge, a sensor to receive reflections from capping layers disposed about the microfluidic feature in the feature layer, and a controller to determine a depth of the microfluidic feature as a function of the received reflections.

In a further embodiment, an analytical instrument includes a housing, a slot in the housing to register a multiple layer test cartridge in a selected position within the housing, a laser disposed to direct light toward a microfluidic cuvette disposed in a feature layer of a multiple layer test cartridge registered in the slot, a sensor to receive reflections from capping layers disposed about the microfluidic cuvette in the feature layer and provide an output signal representative of the received reflections, and a calibrator coupled to the sensor to receive the output signal and determine a calibration to be applied to a measurement of a sample in the microfluidic cuvette as a function of the output signal.

A method includes inserting a multiple layer microfluidic test cartridge into a analytical instrument, measuring a depth of a microfluidic feature in a feature layer in the multiple layer microfluidic test cartridge via an optical sensor in the analytical instrument, and calibrating the analytical instrument for a volume of the microfluidic feature.

DETAILED DESCRIPTION

In the following description, reference is made to the accompanying drawings that form a part hereof, and in which is shown by way of illustration specific embodiments which may be practiced. These embodiments are described in sufficient detail to enable those skilled in the art to practice the invention, and it is to be understood that other embodiments may be utilized and that structural, logical and electrical changes may be made without departing from the scope of the present invention. The following description of example embodiments is, therefore, not to be taken in a limited sense, and the scope of the present invention is defined by the appended claims.

The functions or algorithms described herein may be implemented in software or a combination of software and human implemented procedures in one embodiment. The software may consist of computer executable instructions stored on computer readable media such as memory or other type of storage devices. Further, such functions correspond to modules, which are software, hardware, firmware or any combination thereof. Multiple functions may be performed in one or more modules as desired, and the embodiments described are merely examples. The software may be executed on a digital signal processor, ASIC, microprocessor, or other type of processor operating on a computer system, such as a personal computer, server or other computer system.

An analytical instrument is used to measure samples in microfluidic features of a multiple layer microfluidic disposable test cartridges. The cartridges are registered into the analytical instrument and a fluid is moved into various microfluidic features such as cuvettes, and measured with the analytical instrument. Geometric variability in the cartridges due to manufacturing tolerances can result in inaccurate measurements.

A system and method is used to calibrate the analytical instrument to each cartridge that is inserted for measurements. The calibration may be used to increase the accuracy of tests without the need for extraordinarily tight manufacturing tolerance in forming the microfluidic features. In various embodiments, cuvette thickness is quantified within the analytical instrument for each disposable cartridge, in-situ, by direct measurement of multi-layer features.

Figure 1:
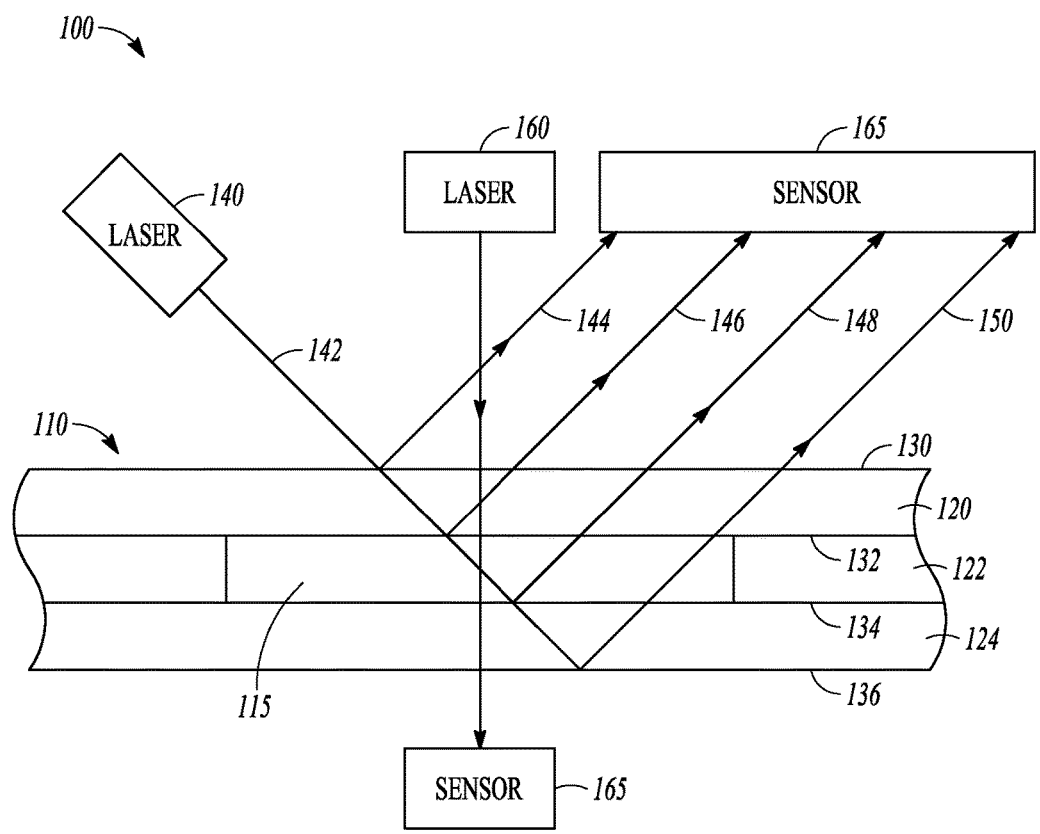
FIG. 1 is a block schematic diagram of an analytical instrument to calibrate and test a multiple layer test cartridge according to an example embodiment.

FIG. 1 is a block schematic diagram of an analytical system 100 for calibrating a cartridge 110 having a microfluidic feature 115. In one embodiment, the feature 115 is a cuvette for holding a sample to be tested. Three layers, 120, 122, 124 are illustrated, with feature 115 formed by cutting out a portion of layer 122, and capped by layers 120 and 124. The layers each have top and bottom surfaces that serve as reflectors of light as shown at 130, 132, 134, and 136.

A laser 140 or other light source may be used to direct light at an angle other than orthogonal in one embodiment toward the cartridge 110 when registered with respect to the laser 140. Light from a laser is indicated at 142, and reflects from each interface as seen by rays 144, 146, 148, and 150. The light is received by a photo detector array that measures the spacing between the rays, which may be converted into a depth of the feature.

In one embodiment, the spacing, or the depth derived from the spacing may be used to derive a calibration value or factor for use when testing is performed. A second laser 160 may be provided to shine light through the feature 115 that contains a sample. The light proceeds through the cartridge 110 and may be measured by a sensor 165, such as a photo detector.

In operation, one example method includes use of the laser 140 and photo-detector array, which are supported in an analytical instrument. The laser 140 is shined at an angle to the surface of the cartridge 110 and its multi-layer stack. The resulting reflections 144, 146, 148, 150 are mapped to the photo-detector array whereby the offset of the reflection is matched, through application of Snell's Law, to the thickness of each layer, providing that the index of refraction for each layer is known.

Figure 2:
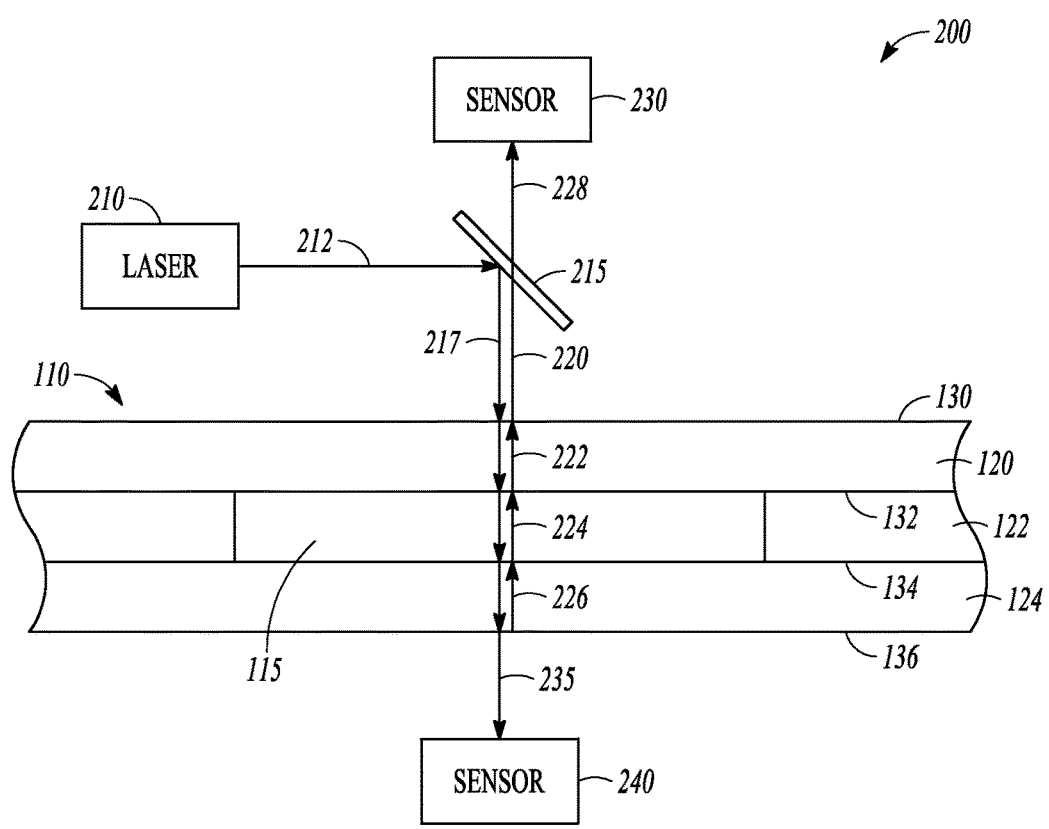
FIG. 2 is a block schematic diagram of an alternative analytical instrument to calibrate and test a multiple layer test cartridge according to an example embodiment.

FIG. 2 is a block schematic diagram of an alternative analytical system 200 for calibrating cartridge 110, which is numbered the same as in FIG. 1. A laser 210 is positioned to project laser light as indicated by a ray 212 that reflects off a mirror 215 and continues toward cartridge 110 as indicated by ray 217. Each surface and meeting of surfaces reflects a portion of the projected light back toward the mirror 215 as indicated by rays 220, 222, 224, and 226. The light projected back toward the mirror 215 passes through the mirror as indicated at 228 toward a sensor 230, such as an interferometer.

In one embodiment, the light is substantially orthogonal (perpendicular) to the surfaces. While the ray and reflections are indicated as offset from each other, the offset is used for convenience of illustration. In reality, the rays may follow the same or substantially the same path. Sensor 230 in one embodiment comprises an interference detector, e.g. Fabry-Perot interferometer, to scan the fringes of the reflections.

To measure the sample, laser 210 may also be utilized with mirror 215 to project light all the way through the cartridge 110 as indicated at ray 235 to a sensor 240. Sensor 240 may also be a photo detector.

Figure 3:
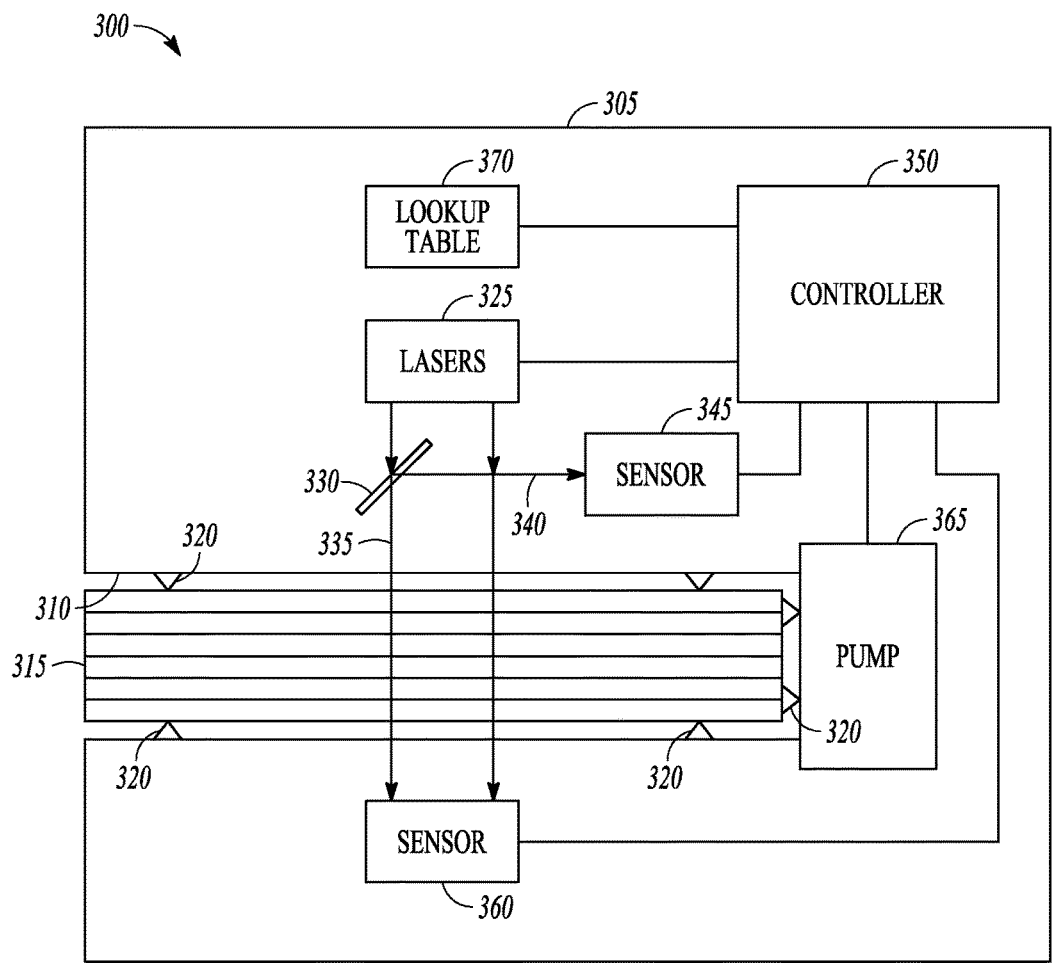
FIG. 3 is a block schematic diagram of an analytical instrument to register, calibrate, and test a multiple layer test cartridge according to an example embodiment.

FIG. 3 is a block schematic diagram of an analytical system 300. Analytical system 300 includes a case 305 having a slot 310 to receive a test cartridge 315. Registration features indicated at 320 may be used for example to register the cartridge 315 into the analytical instrument slot 310. Keying features may also be used to ensure proper orientation of the cartridge 315 in the slot 310.

One or more lasers 325 may be positioned in the case 305 to project light toward the inserted and registered cartridge 315 through a mirror 330. As projected light indicated at 335 encounters layers of the cartridge 315, it is reflected back, and again reflected by the mirror 330 as indicated at 340 toward a sensor 345.

A controller 350 is utilized to control the lasers 325 to project light at appropriate times, and to receive data from sensor 345. The controller 350 is also coupled to a sensor 360 and a pump 365. In operation, the lasers 325 also project light through the test feature or features of the cartridge 315. The projected light is sensed by sensor 360, with a signal from the sensor 360 provided to controller 350. The sensor 350 may also be used to control pump 365 which is coupled to the cartridge microfluidics to provide pressure, such as vacuum to move fluid into the microfluidic features to be measured, following calibration of such features. In one embodiment, a calibration value or values may be calculated utilizing an algorithm, or a lookup table 370. Following determination of the calibration value or values, the controller may then cause fluid to be moved to the features and tested. The calibration value or values are then applied to initial test results to provide final test results.

Analytical system 300 may utilize either type of calibration described above in various embodiments. Further configurations of lasers and detectors may be used in further embodiments. In one embodiment, multiple portions of the microfluidic feature may be tested to determine multiple spaced apart depths of the features. The multiple depths may be averaged to determine the volume of the feature and hence the calibration value. In further embodiments, the depth is measured at the same point as the measurement will be taken to determine the calibration value.

Figure 4:
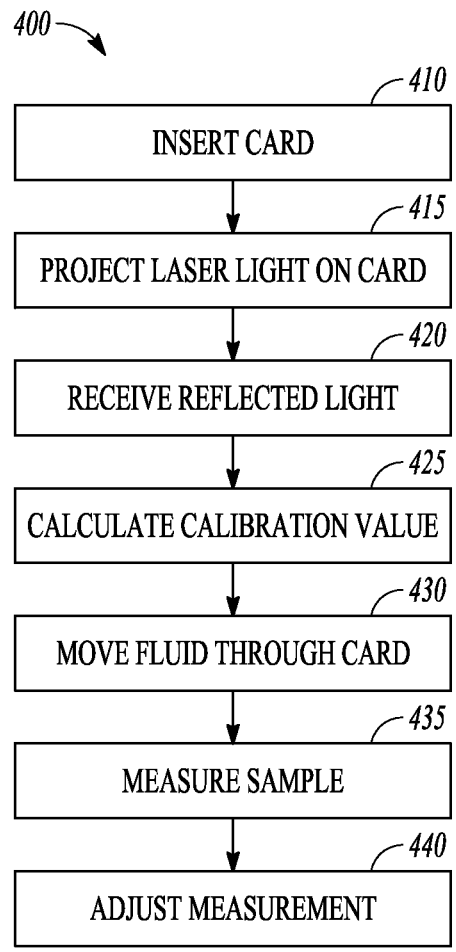
FIG. 4 is a flowchart illustrating a method of calibrating and testing a multiple layer test cartridge according to an example embodiment.

FIG. 4 is a flowchart illustrating a method 400 of calibrating and testing a multiple layer test cartridge according to an example embodiment. At 410, the cartridge, also referred to as a cartridge, is inserted and registered in the analytical instrument. At 415, laser light is projected toward the surfaces of the test cartridge. The reflections from multiple surfaces of the layers of the test cartridge are received at 420. A calibration value or values are calculated at 425. The calibration is performed without fluid in the microfluidic features that are measured in one embodiment. Following calibration, fluid is moved at 430 through many microfluidic channels and features. The fluid may be processed to perform one or multiple tests. The fluid may be separated into different constituents with various reagents added, and used to fill one or more cuvettes.

Once the fluid is in selected cuvettes, the samples may be tested, and sensed values provided at 435. The calibration may then to used to adjust the sensed values at 440 to account for different sized cuvettes permitted by design tolerances. By using the calibration, tolerances need be relaxed, enabling high manufacturing and assembly yields.

Figure 5:
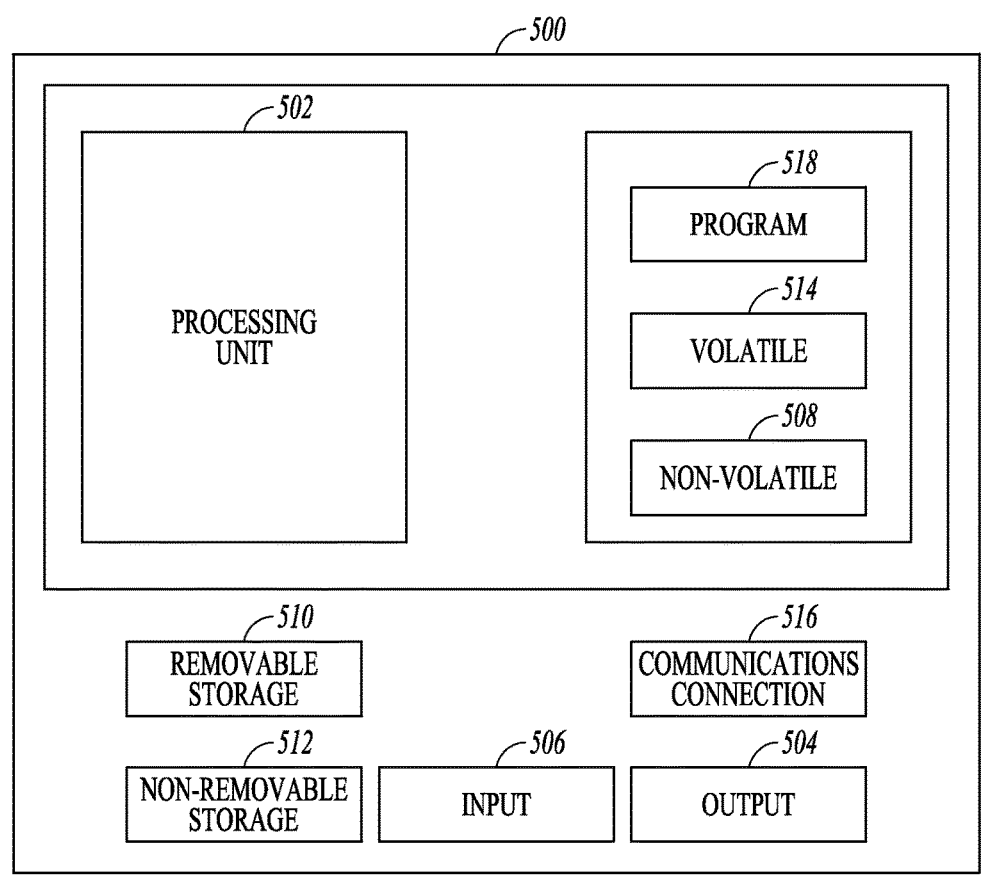
FIG. 5 is a block schematic diagram of a computer system to implement a controller according to an example embodiment.

FIG. 5 is a block schematic diagram of a computer system 500 to implement a controller according to an example embodiment. In one embodiment, multiple such computer systems are utilized in a distributed network to implement multiple components in a transaction based environment. An object-oriented, service-oriented, or other architecture may be used to implement such functions and communicate between the multiple systems and components. One example computing device in the form of a computer 500 may include a processing unit 502, memory 503, removable storage 510, and non-removable storage 512. Memory 503 may include volatile memory 514 and non-volatile memory 508. Computer 500 may include—or have access to a computing environment that includes—a variety of computer-readable media, such as volatile memory 514 and non-volatile memory 508, removable storage 510 and non-removable storage 512. Computer storage includes random access memory (RAM), read only memory (ROM), erasable programmable read-only memory (EPROM) & electrically erasable programmable read-only memory (EEPROM), flash memory or other memory technologies, compact disc read-only memory (CD ROM), Digital Versatile Disks (DVD) or other optical disk storage, magnetic cassettes, magnetic tape, magnetic disk storage or other magnetic storage devices, or any other medium capable of storing computer-readable instructions. Computer 500 may include or have access to a computing environment that includes input 506, output 504, and a communication connection 516. The computer may operate in a networked environment using a communication connection to connect to one or more remote computers, such as database servers. The remote computer may include a personal computer (PC), server, router, network PC, a peer device or other common network node, or the like. The communication connection may include a Local Area Network (LAN), a Wide Area Network (WAN) or other networks.

Computer-readable instructions stored on a computer-readable medium are executable by the processing unit 502 of the computer 500. A hard drive, CD-ROM, and RAM are some examples of articles including a non-transitory computer-readable medium. For example, a computer program 518 capable of providing a generic technique to perform access control check for data access and/or for doing an operation on one of the servers in a component object model (COM) based system may be included on a CD-ROM and loaded from the CD-ROM to a hard drive. The computer-readable instructions allow computer 500 to provide generic access controls in a COM based computer network system having multiple users and servers.

The present subject matter can be described by way of several examples.

Example 1 can include or use subject matter (such as an apparatus, a method, a means for performing acts, or a device readable memory including instructions that, when performed by the device, can cause the device to perform acts), such as can include or use (1) inserting a multiple layer microfluidic test cartridge into an analytical instrument, (2) measuring a depth of a microfluidic feature in a feature layer in the multiple layer microfluidic test cartridge via an optical sensor in the analytical instrument, or (3) calibrating the analytical instrument for a volume of the microfluidic feature Example 2 can include or use, or can optionally be combined with the subject matter of Example 1, to include or use, wherein calibrating the analytical instrument comprises determining a calibration value to be used in a measurement of a sample in the microfluidic feature.

Example 3 can include or use, or can optionally be combined with the subject matter of Example 2, to include or use, wherein the calibration value is determined from a lookup table.

Example 4 can include or use, or can optionally be combined with the subject matter of at least one of Examples 1-3, to include or use, wherein the measured depth is a depth of cuvette defined in the feature layer of the microfluidic test cartridge.

Example 4 can include or use, or can optionally be combined with the subject matter of at least one of Examples 1-3, to include or use the measured depth is a depth of cuvette defined in the feature layer of the microfluidic test cartridge.

Example 5 can include or use, or can optionally be combined with the subject matter of at least one of Examples 1-4, to include or use, wherein measuring the depth of the microfluidic feature comprises mapping angled reflections of laser light from the microfluidic feature onto a photodetector array.

Example 6 can include or use, or can optionally be combined with the subject matter of Example 5, to include or use, wherein the angled reflections comprise reflections from adjacent layers capping the microfluidic feature in the feature layer.

Example 7 can include or use, or can optionally be combined with the subject matter of Example 6, to include or use, wherein the angled reflections are matched to determine the depth via application of Snell's law.

Example 8 can include or use, or can optionally be combined with the subject matter of at least one of Examples 1-7, to include or use, wherein measuring the depth of the microfluidic feature comprises sensing reflections of a laser directed orthogonal to the microfluidic feature, and detecting interference in reflections from the microfluidic feature.

Example 9 can include or use, or can optionally be combined with the subject matter of Example 8, to include or use, wherein the reflections comprise reflections from adjacent layers capping the microfluidic feature in the feature layer.

Example 10 can include or use, or can optionally be combined with the subject matter of at least one of Examples 1-9, to include or use moving fluid through multiple microfluidic structures, performing a measurement on a sample from the fluid in the microfluidic feature, and adjusting the measurement as a function of the calibration.

Example 11 can include or use subject matter (such as an apparatus, a method, a means for performing acts, or a device readable memory including instructions that, when performed by the device, can cause the device to perform acts), such as can include or use an analytical instrument comprising a laser disposed to direct light toward a microfluidic feature disposed in a feature layer of a multiple layer test cartridge, a sensor to receive reflections from capping layers disposed about the microfluidic feature in the feature layer, and a controller to determine a depth of the microfluidic feature as a function of the received reflections.

Example 12 can include or use, or can optionally be combined with the subject matter of Example 11, to include or use, wherein the controller is programmed to determine a calibration value to be used in a measurement of a sample in the microfluidic feature.

Example 13 can include or use, or can optionally be combined with the subject matter of Example 11, to include or use, wherein the calibration value is determined from a lookup table.

Example 14 can include or use, or can optionally be combined with the subject matter of at least one of Examples 11-13, to include or use, wherein the measured depth is a depth of cuvette defined in the feature layer of the microfluidic test cartridge.

Example 15 can include or use, or can optionally be combined with the subject matter of at least one of Examples 11-14, to include or use, wherein the laser is disposed to direct light at a non-orthogonal angle to the feature layer and the sensor comprises a photo detector array positioned to receive light reflected from the feature.

Example 16 can include or use, or can optionally be combined with the subject matter of at least one of Examples 11-15, to include or use, wherein the laser is disposed to direct light orthogonal to the microfluidic feature, and the sensor is disposed to detect interference in reflections from the microfluidic feature.

Example 17 can include or use, or can optionally be combined with the subject matter of Example 16, to include or use, wherein the reflections comprise reflections from adjacent layers capping the microfluidic feature in the feature layer.

Example 18 can include or use, or can optionally be combined with the subject matter of at least one of Examples 11-17, to include or use, analytical instrument of any of examples 11-17a vacuum source to couple to the test cartridge and move fluid through multiple microfluidic structures, a light source disposed to perform a measurement on a sample from the fluid in the microfluidic feature, and wherein the controller adjusts the measurement as a function of the calibration.

Example 19 can include or use subject matter (such as an apparatus, a method, a means for performing acts, or a device readable memory including instructions that, when performed by the device, can cause the device to perform acts), such as can include or use an analytical instrument comprising a housing, a slot in the housing to register a multiple layer test cartridge in a selected position within the housing, a laser disposed to direct light toward a microfluidic cuvette disposed in a feature layer of a multiple layer test cartridge registered in the slot, a sensor to receive reflections from capping layers disposed about the microfluidic cuvette in the feature layer and provide an output signal representative of the received reflections, and a calibrator coupled to the sensor to receive the output signal and determine a calibration to be applied to a measurement of a sample in the microfluidic cuvette as a function of the output signal.

Example 20 can include or use, or can optionally be combined with the subject matter of Example 19, to include or use, wherein the laser is disposed to direct light orthogonal to the microfluidic cuvette, and the sensor is disposed to detect interference in reflections from the microfluidic cuvette wherein the reflections comprise reflections from adjacent layers capping the microfluidic feature in the feature layer.

Although a few embodiments have been described in detail above, other modifications are possible. For example, the logic flows depicted in the figures do not require the particular order shown, or sequential order, to achieve desirable results. Other steps may be provided, or steps may be eliminated, from the described flows, and other components may be added to, or removed from, the described systems. Other embodiments may be within the scope of the following claims.

The invention claimed is:

1. An analytical instrument comprising:
a microfluidic feature including a top capping layer on a first side of the microfluidic feature and a bottom capping layer on a second, opposite side of the microfluidic feature, the microfluidic feature disposed in a feature layer of a multiple layer test cartridge;
a first laser disposed to direct light toward the top capping layer of the microfluidic feature;
a first sensor disposed on the first side of the microfluidic feature to receive reflections from the top and bottom capping layers;
a second sensor disposed on the second side of the microfluidic feature to receive light that passes through the top capping layer, the microfluidic feature, and the bottom capping layer and produce a pass-through value based on the received light; and
a controller to determine a depth of the microfluidic feature as a function of the received reflections and the pass-through value.

2. The analytical instrument of claim 1 wherein the controller is programmed to determine a calibration value based on the depth of the microfluidic feature, the calibration value to be used in a measurement of a sample in the microfluidic feature.

3. The analytical instrument of claim 2 wherein the calibration value is determined from a lookup table.

4. The analytical instrument of claim 1, wherein the microfluidic feature includes a cuvette and wherein the measured depth is a depth of the cuvette of the test cartridge.

5. The analytical instrument of claim 1 wherein the laser is disposed to direct light at a non-orthogonal angle to a top surface of the top capping layer and the first sensor comprises a photo detector array positioned to receive light reflected from the top capping layer and the bottom capping layer, wherein the reflections from the top and bottom capping layer are spaced apart in a direction generally perpendicular to a depth of the microfluidic feature, and wherein the controller determines the depth of the microfluidic feature based on a calculated distance between the top and bottom capping layers, the distance calculation based on the index of refraction of the top and bottom capping layers, the microfluidic feature, and the distance the reflection from the top and bottom capping layers are spaced apart; and
the analytical instrument further comprises a light source disposed to direct light to the top capping layer at an angle orthogonal to the top surface of the top capping layer, through the top capping layer, the microfluidic feature, and the bottom capping layer to the second sensor.

6. The analytical instrument of claim 1, further comprising a mirror disposed in front of the first laser to redirect light from the first laser to be orthogonal to the top surface of the top capping layer, and the first sensor is an interferometer disposed to detect interference in reflections from the microfluidic feature.

7. The analytical instrument of claim 2 and further comprising:
a vacuum source coupled to the test cartridge to move fluid through microfluidic feature;
a light source disposed to direct light generally orthogonal to a top surface of the top capping layer and onto a sample in the microfluidic feature; and
wherein the controller adjusts the measurement of the sample as a function of the calibration, wherein the measurement of the sample is based on data received from the second sensor.

8. An analytical instrument comprising:
a housing;
a multiple layer test cartridge including a top capping layer, a bottom capping layer, and a microfluidic cuvette, the top capping layer on a first side of the and the bottom capping layer on a second side of the microfluidic cuvette opposite the first side;
a slot in the housing to register the multiple layer test cartridge in a selected position within the housing;
a laser disposed to direct light toward the top capping layer;
a first sensor disposed on the first side of the microfluidic cuvette to receive reflections from the top and bottom capping layers provide an output signal representative of the received reflections;
a second sensor disposed on the second side of the microfluidic cuvette to receive light that passes through the top capping layer, microfluidic cuvette, and the bottom capping layer and provide a measurement of a sample disposed in the microfluidic cuvette; and
a calibrator coupled to the first and second sensors to receive the output signal, determine a depth of the microfluidic cuvette based on the output signal, and adjust the determined depth based on the measurement.

9. The analytical instrument of claim 8 wherein the laser is disposed to direct light at a non-orthogonal angle to a top surface of the top capping layer, and the first sensor comprises a photo detector array positioned to receive light reflected from the top capping layer and the bottom capping layer, wherein the reflections from the top and bottom capping layer are spaced apart in a direction generally perpendicular to a depth of the microfluidic feature, and wherein the controller determines the calibration based on the depth of the microfluidic cuvette, the depth of the microfluidic cuvette determined by the controller based on a calculated distance between the top and bottom capping layers, the distance calculation based on the index of refraction of the top and bottom capping layers, the feature layer, and the distance the reflection from the top and bottom capping layers are spaced apart; and
the analytical instrument further comprises a light source disposed to direct light to the top capping layer at an angle generally orthogonal to the top surface of the top capping layer, through the top capping layer, the microfluidic feature, and the bottom capping layer to the second sensor.

10. The analytical instrument of claim 1 further comprising:
- a pump configured to push a fluid into the microfluidic feature; and
- wherein the controller is configured to determine a depth of the microfluidic feature using reflections received prior to the pump pushing fluid into the microfluidic feature and the controller is configured to adjust the determined depth of microfluidic feature using the received light after the pump has pushed the fluid into the microfluidic feature.

11. The analytical instrument of claim 8 further comprising:
- a pump configured to push a fluid into the microfluidic cuvette; and
- wherein the calibrator is configured to determine the prior to the pump pushing fluid into the microfluidic cuvette and the controller is configured to adjust the determined depth of microfluidic cuvette using the received light after the pump has pushed the fluid into the microfluidic cuvette.

\* \* \* \* \*